United States Patent [19]

Lush

[11] Patent Number: 4,992,275

[45] Date of Patent: * Feb. 12, 1991

[54] SWEET CORN BASED PESTICIDE

[76] Inventor: Raymon W. Lush, 113 Crown Point, Bloomfield, Nebr. 68718

[*] Notice: The portion of the term of this patent subsequent to Mar. 28, 2006 has been disclaimed.

[21] Appl. No.: 373,564

[22] Filed: Jun. 30, 1989

[51] Int. Cl.⁵ .................. A01N 25/34; A01N 25/00; A01N 25/08; A01N 55/02

[52] U.S. Cl. .................. 424/408; 424/409; 424/405; 424/410; 514/188; 435/832

[58] Field of Search .............. 424/410, 409, 405, 408, 424/195.1; 435/832; 514/188

[56] References Cited

U.S. PATENT DOCUMENTS

| | | | |
|---|---|---|---|
| 2,687,365 | 7/1951 | Link | 424/410 |
| 2,770,067 | 7/1952 | Lindblom | 424/410 |
| 3,252,785 | 5/1966 | Hoblit | 71/3 |
| 3,272,696 | 9/1966 | O'Connell | 424/DIG. 12 |
| 3,272,698 | 9/1966 | Lemin | 424/DIG. 12 |
| 3,496,272 | 2/1970 | Kruger | 424/410 |
| 4,049,460 | 9/1977 | Broadbent | 514/89 |
| 4,440,746 | 4/1984 | Maglio | 424/78 |
| 4,815,923 | 3/1989 | Lush | 514/457 |
| 4,834,977 | 5/1989 | Kohama | 424/405 |

FOREIGN PATENT DOCUMENTS

| | | |
|---|---|---|
| 0228228 | 7/1987 | European Pat. Off. . |
| 59-067209 | 4/1984 | Japan . |
| 85/04074 | 9/1985 | PCT Int'l Appl. . |

Primary Examiner—Lester L. Lee
Assistant Examiner—Carmen Pili-Curtis
Attorney, Agent, or Firm—John A. Beehner

[57] ABSTRACT

A pesticidal composition includes an active ingredient mixed with an inert ingredient comprising dried sweet corn as a substantial portion thereof. The dried sweet corn is preferably ground, mixed with the active ingredient and then provided in pelleted, granular or meal form.

13 Claims, No Drawings

SWEET CORN BASED PESTICIDE

BACKGROUND OF THE INVENTION

The present invention is directed generally to a new pesticidal composition, other than a rodenticidal composition, which is a mixture of raw dried sweet corn as a natural palatable inert ingredient and an effective active ingredient. The invention may be an insecticidal composition, a nematicidal composition, or a miticidal composition upon use of an insecticide, nematicide and miticide, respectively, as the active ingredient.

Applicant is the owner of U.S. Pat. No. 4,815,923, issued Mar. 28, 1989, entitled Sweet Corn Based Rodenticide. Efficacy tests of the patented rodenticide have shown it to be an effective and commercially significant product. Much of the effectiveness is attributed to the use of mature dried sweet corn as a substantial portion of the inert ingredient thereof. The inert sweet corn ingredient has proven to be a superior attractant.

Rodents are only one form of pest which pesticides are formulated to exterminate. Other pests include insects, nematodes and mites for which specific pesticides are provided and referred to as insecticides, nematicides and mitacides, respectively.

These and other types of pests cause substantial economic problems for agriculture, and, therefore, the public generally, if not controlled. Pesticides are a significant cost factor for crop producing farmers. The effectiveness and resultant cost efficiency of a given pesticide are controlling factors in pesticide selection. Crop losses in fields infested with insects, nemitodes or mites often make the difference between a profit and loss for a particular crop. Diseases transmitted by pests endanger the health of infested animals. Finally, uncontrolled infestations of pests generally results in further proliferation of the pests and a worsening of the problems associated with them.

One method of controlling a pest population is by using pesticides. Many different pesticides have been devised and made commercially available to date. A pesticide includes an inert food base, an active ingredient and various additives. Such grains as field corn and oats have been used as ingredients of pesticide food bases. "Field corn", or the botanical term Zea Mays is intended to refer to the various types of grains which are normally grown for feeding livestock, such as yellow dent corn, flint corn and soft corn and, in some cases, grain sorghum. Likewise, field corn is to be distinguished from the vegetable sweet corn which is referred to by its botanical name Zea Mays Saccharata and by International Feed No. 40297.

Known pesticides have certain limitations, however, relating primarily to effectiveness and stability. Vegetables generally have been considered as unsuitable ingredients for pesticides because of short shelf life. Pesticides are typically subjected to storage stability tests wherein a batch of the pesticide is tested periodically such as monthly over a one (1) year period to determine if the food base is shelf stable and if the active ingredient is still active.

Pesticide acceptance depends upon a combination of texture, taste and odor. Whereas, odor can help attract certain pests to a bait, the final test of consumption is the palatability of the material determined by its taste and texture.

A common solution for improving pesticides is to include additives. Additives may be included for many different reasons which often result in increased acceptance of the pesticide. Additives may include an odor-producing attractant, binders for holding the bait particles together, coloring agents, emetics for causing non-target animals to regurgitate the bait, enhancers such as sugar, preservatives and, to a limited extent, potentiating agents. Such additives may increase manufacturing costs without an attendant increase in the acceptance rate for the pesticide product.

Accordingly, a primary object of the present invention is to provide an improved pesticidal composition.

Another object is to provide a pesticidal composition which is highly effective for pest control.

Another object is to provide such an improved pesticidal composition in the form of insecticidal, nematicidal and miticidal compositions.

Another object is to provide a pesticidal composition which is simple and economical to formulate and produce.

Another object is to provide a pesticidal composition which uses dried natural sweet corn as the inert ingredient thereof.

Another object is to provide a highly effective pesticidal composition which is free of additives.

Another object is to provide a relatively safe pesticidal composition for which a known antidote is available for the active ingredient thereof.

Finally, an object of the invention is to provide an improved pesticidal composition which is simple in formulation, economical to produce an effective in operation.

SUMMARY OF THE INVENTION

The improved pesticidal composition of the present invention includes an active ingredient mixed with an inert ingredient including natural raw, dried sweet corn as a substantial portion thereof. Preferably the sweet corn is dried down to a dented state, either in the field or by artificial means after harvesting. The dried sweet corn is then ground and mixed with an active ingredient such as Chlorpyrifos and either pelleted, granulated or provided in the form of meal.

Pesticidal compositions including dried natural raw sweet corn as the inert ingredient thereof may be provided as insecticidal, nemitacidal and miticidal compositions, among others. Whereas, sweet corn may be economically produced, additional economics are achieved because the dried sweet corn based pesticidal composition requires no expensive additives. The effectiveness of the active ingredient of the pesticidal composition is greatly enhanced by the high acceptability of raw sweet corn which assured that sufficient quantities of the pesticide will be consumed for effective pest control.

DESCRIPTION OF THE PREFERRED EMBODIMENT

The improved pesticide of the present invention is a mixture of an active ingredient with an inert ingredient including raw dried sweet corn as the substantial portion thereof. The term "pesticidal composition" is intended to be broadly construed to include, among others, insecticidal, nematicidal and miticidal compositions, but to exclude rodenticidal compositions which are the subject matter of applicant's issued U.S. Pat. No. 4,815,923. Whereas, the term "pesticide" is commonly used to refer to the overall pesticidal composition, it is used herein to refer to the active ingredient thereof which may be, among others, an insecticide, nematicide or miticide.

Zea Mays Saccharata is the botanical name for the vegetable sweet corn which is also referred to by International Feed No. 40297. Sweet corn is normally grown for human consumption and is harvested in the ear while the kernel is in the relatively soft and moist milk stage. The soft and moist sweet corn has limited utility for a pesticide because of its short shelf life due to spoilage and the difficulty of handling, dividing and mixing the soft and moist kernels.

For use in the present invention, however, sweet corn is dried down to a dented state. Dried sweet corn herein refers to sweet corn having a moisture content of fifteen percent (15%) or less. A moisture content of ten percent (10%) or below is preferred.

The sweet corn may be planted and cultivated in the same manner as field corn and is left in the field to mature past the milk stage, which is the normal harvest period for sweet corn. It is left in the field to mature as long as possible to allow maximum dry down of the kernel before ear droppage and stalk lodging occurs to the point that it is no longer economically feasible to harvest.

The dried sweet corn is then ground to a fine ground condition which is not nearly as fine as flour, for example. "Grinding" herein collectively refers to such processes as crushing, grinding, rolling or otherwise reducing the kernel to a smaller particle size, with the end result hereinafter referred to as ground sweet corn. A double grinding process is preferred for a more uniform particle size in the dried ground sweet corn.

The ground sweet corn is then mixed with an active ingredient so as to be effective as a pesticidal composition. A preferred active ingredient for an insecticidal composition is the insecticide Basillus thuringiensis, var. kurstaki having 1,600 International Units of potency per milligram. A preferred proportion of this active ingredient is 0.32% by weight with the remaining 99.68% being the inert ingredient.

The mixture may be provided in various forms including pelleted, granular and meal. The pellet size may be varied but an acceptable size is a 3/16" diameter pellet with approximately seven pellets per gram or 196 pellets per ounce. The pellet diameter is preferably between three and six millimeters. The granular form of the insecticidal composition would be crumbled having particle sizes somewhat smaller than the pellets, with most particles having a size which falls within the range of between 0.5 and 1.5 millimeters. The meal form of the insecticidal composition would have a somewhat flour-like consistency much like the ground composition prior to pelleting.

Application of the insecticidal composition may include distribution with ground equipment, by hand-throwing or aerial application. This insecticidal composition is particularly suitable for control of European corn borer (Ostrinia Nubilalis) first generation larvae on seed corn, field corn, popcorn and sweet corn. The preferred application rate is ten pounds (10 lbs.) per acre.

The insecticidal composition should be applied directly to corn whorls. Seed corn should be treated when twenty-five percent (25%) of the plants show shot hole feeding in the whorls and field corn should be treated when thirty-five percent (35%) of the whorls show feeding. At that stage, larvae are likely to be small and present. Satisfactory control cannot be expected after higher injury levels to the whorls or after larvae have begun stalk boring.

Since the insecticide of this composition is a stomach poison, it, therefore, must be eaten by larvae to be effective. Accordingly, it is preferred that the insecticidal composition be distributed in a layer or zone through a field that insects have to migrate through. Extreme climate such as heavy rain or strong winds shortly after treatment may cause the insectidal composition to be removed from the feeding zone, making retreatment necessary.

A second example of an insecticidal composition of the present invention includes the active ingredient Chlorpyrifos [O, O-diethyl, O-(3, 5, 6 -trichloro-2 -pyridyl phosphorothioate)] in a preferred concentration of fifteen percent (15%) by weight, as compared to eighty-five percent (85%) inert ingredient.

| | | APPLICATION RATE Per 1,000 Feet of Row | | | | PER ACRE |
|---|---|---|---|---|---|---|
| | | At Planting Time | | | After | Pre-plant Broad- |
| CROP | INSECT | T-band | Band | In-Furrow | Planting | cast |
| Corn Field, Popcorn, Sweet Corn | Northern, Southern and Western Corn Rootworm Larvae | 8 oz | | | 8 oz | |
| | Cutworms | 8 oz | 8 oz | 8 to 16 oz | | 6.75 to 13.5 lb |
| | Wireworms | 8 to 16 oz | 16 oz | 8 to 16 oz | | 13.5 lb |
| | Billbugs | 8 to 16 oz | 8 to 16 oz | — | — | 13.5 lb |
| | Seed Corn Maggots | 8 oz | — | 8 oz | — | — |
| | Grubs | 16 oz | — | 8 to 16 oz | — | 13.5 lb |
| | Lesser Cornstalk Borer | 8 to 16 oz | 8 to 16 oz | — | — | — |
| | Seed Corn Beetle | 8 to 16 oz | — | 8 oz | — | — |

-continued

| | | APPLICATION RATE Per 1,000 Feet of Row | | | | PER ACRE Pre-plant Broad-cast |
|---|---|---|---|---|---|---|
| | | At Planting Time | | | After Planting | |
| CROP | INSECT | T-band | Band | In-Furrow | | |
| | Flea Beetle Larvae | — | — | — | — | 13.5 lb |
| | Symphylans | 8 to 16 oz | 8 to 12 oz | — | — | — |
| | European and Southwestern Corn Borer | — | — | — | 6 to 8 oz | — |
| Citrus Orchard Floors | Fire Ants, and other ant species | — | — | — | 6.7 lb/A | — |
| Grain Sorghum | Lesser Cornstalk Borer | 4 to 12 oz | 4 to 12 oz | — | — | — |
| | Corn Rootworm and Cutworms | 8 oz | 8 oz | — | — | — |
| Onions (Dry Bulb) | Onion Maggot | — | | 3.7 oz | — | — |
| Peanuts | Cutworms, Lesser Cornstalk Borer, Southern Corn Rootworm Larvae, Southern Blight (White Mold) | — | — | — | 15 oz | — |
| | Lesser Cornstalk Borer | — | — | — | 7.5 to 15 oz | — |
| Soybeans | Lesser Cornstalk Borer, Cutworms | 8 oz | 8 oz | — | 8 oz | — |
| Sugarbeets | Sugarbeet Root Maggot | 6.5 oz 9.0 oz | 6.5 9.0 | 4.5 to 9.0 oz | 6.5 to 9.0 oz | — |
| | Cutworms | 6.5 to 9.0 oz | 6.5 8 oz | — | — | — |
| Sunflowers | Cutworms | — | 8 oz | — | — | — |
| Sweet Potatoes | Wireworms (Conoderus) Flea Beetles (Systena) and Sweetpotato Beetle | — | | | | 13.5 to 20 lb |
| Tobacco | Cutworms, Flea Beetle Larvae, Root Maggots, and Wireworms | — | — | — | — | 13.5 to 20 lb |
| Vegetables | | | | | | |
| Broccoli, Brussels Sprouts, Cabbage, Cauliflower Chinese Cabbage, Collards, Kale, | Root Maggots | 4.6 9.2 | — | — | — | — |

| | | APPLICATION RATE Per 1,000 Feet of Row | | | | PER ACRE Preplant Broadcast |
|---|---|---|---|---|---|---|
| | | At Planting Time | | | After | |
| CROP | INSECT | T-band | Band | In-Furrow | Planting | |
| Kohlrabi, Rutabagas, Turnips Radishes | Root Maggots | — | — | 3.3 oz | — | — |

A third example of a pesticidal composition of the present invention, primarily for the control of sweet eating ants, includes sodium arsenate as the active ingredient thereof in a proportion by weight of 2.27% to 97.3% for the inert ingredient. Grease ants may not be attracted to this embodiment.

The pesticidal composition of the present invention is effective despite the very simple formulation, including only two (2) ingredients, namely a respective active ingredient and dried sweet corn as the inert ingredient. Pesticides typically include multiple grains, oils and sugars. Natural raw sweet corn is efficiently high in oil and sugar contents so as to eliminate the need for such additives. In this connection, it is preferred that the sweet corn be used in a raw state, meaning unprocessed. Cooking processes, such as roasting, alter the starch content by converting some starches to sugar, resulting in an over sweet pesticide with diminished acceptance by pests.

Whereas, the invention has been described herein in connection with the preferred embodiments thereof, it is understood that many modifications, additions and substitutions may be made, which are within the intended broad scope of the appended claims. The relative proportion of active ingredient to inert ingredient is a matter well within the skill of the art. Accordingly, it is submitted that the term "a substantial portion thereof" is definite and proper in the context of the present invention.

Regarding the proportion of sweet corn to other ingredients in the inert ingredient or attractant, it would appear that "the more, the better" would apply. Nevertheless, it is fully expected that one can achieve some benefits of the invention even if the dried sweet corn is mixed with other inert ingredients.

The invention is limited to pesticidal compositions including dried sweet corn as a substantial portion of the inert ingredient so as to exclude those pesticidal compositions wherein the proportion of sweet corn may be so small as to be inconsequential.

Other and newly discovered active ingredients may be used in the pesticidal composition of the invention and such compositions may be used for the treatment and extermination of pests other than those specifically described herein.

Thus, there has been shown and described an improved pesticidal composition which accomplishes all of the stated objects.

I claim:
1. An insecticidal composition, comprising,
an effective amount of an insecticide and,
an inert ingredient comprising dried sweet corn as a substantial portion thereof.
2. The composition of claim 1 wherein said inert ingredient is comprised entirely of dried sweet corn.
3. The composition of claim 1 wherein said sweet corn is in a raw state.
4. The composition of claim 3 wherein said inert ingredient is free of additives.
5. The composition of claim 3 wherein said sweet corn is ground, mixed with the insecticide and pelleted.
6. The composition of claim 5 wherein the pelleted insecticide is formed in pellets generally having a diameter between 3 and 6 millimeters.
7. The composition of claim 3 wherein said sweet corn is ground, mixed with insecticide and granulated.
8. The composition of claim 3 wherein said sweet corn is ground, mixed with insecticide and provided as meal.
9. The composition of claim 3 wherein said insecticide is bacillus thuringiensis, var. kurstaki.
10. The composition of claim 3 wherein said insecticide is chlorpyrifos.
11. The composition of claim 3 wherein the insecticide comprises between 0.1 and 25 percent by weight.
12. A nematicidal composition, comprising,
an effective amount of a nematicide, and
an inert ingredient comprising dried sweet corn as a substantial portion thereof.
13. A miticidal composition, comprising,
an effective amount of a miticide, and
an inert ingredient comprising dried sweet corn as a substantial portion thereof.

* * * * *